United States Patent [19]

Haynes et al.

[11] Patent Number: 4,728,660

[45] Date of Patent: Mar. 1, 1988

[54] METHOD OF TREATING DISEASES ARISING FROM PLATELET HYPERACTIVATION

[75] Inventors: Duncan H. Haynes; Wenche Jy; Yeon S. Ahn; William J. Harrington, all of Miami, Fla.

[73] Assignee: University of Miami, Coral Gables, Fla.

[21] Appl. No.: 619,212

[22] Filed: Jun. 11, 1984

[51] Int. Cl.$^4$ .................. A61K 31/455; G01N 33/49; C12Q 1/56

[52] U.S. Cl. ..................................... 514/356; 514/824; 514/929; 435/2; 435/13; 435/29; 436/63

[58] Field of Search ...................... 514/356, 824, 929; 435/2, 13, 29; 436/63

[56] References Cited

U.S. PATENT DOCUMENTS 4,444,778  4/1984  Coughlin ............................ 514/324

OTHER PUBLICATIONS

Pumphrey et al., *Am. J. Cardiol.*, vol. 51, pp. 541–595, Feb. 1983.

Chandler et al., cited in Chem. Abstracts vol. 88:164855a 1978.
Gelmers *Acta Neurol Scand.* 1984:69:232–239.
Henry, cited in Chem. Abstracts vol. 99:32910g 1983.
Henry et al., cited in Chem. Abstracts vol. 98:11308f 1983.

*Primary Examiner*—J. R. Brown
*Assistant Examiner*—Jacqueline M. Stone
*Attorney, Agent, or Firm*—Nixon & Vanderhye

[57] ABSTRACT

Calcium ($Ca^{2+}$) channel blockers, such as nifedipine and verapamil, are used in the treatment of thromboembolic diseases such as stroke and peripheral vascular occlusive diseases, especially arterial and venous thrombosis, vasculitis, myelofibrosis disease and hemolytic anemias. Such diseases arise from platelet hyperactivation and the $Ca^{2+}$ channel blockers restore the platelets to their normal aggregation characteristics. Diagnostic procedures for detecting platelet hyperactivation and defective calcium handling/transport indicative of certain peripheral obstructive diseases using chlorotetracycline as a detectable fluorescent probe as a means of assessing a patient's response to $Ca^{2+}$ channel blockers in the therapy of such diseases are also described.

6 Claims, 8 Drawing Figures

METHOD OF TREATING DISEASES ARISING FROM PLATELET HYPERACTIVATION

BACKGROUND OF THE INVENTION

Current Therapy for Vascular Occlusive Diseases: Thrombosis and many related peripheral obstructive diseases are the result of abnormal activation of normal clotting mechanisms. Normal blood clotting is the result of a highly amplified chain reaction triggered by exposure of soluble factors and platelets to tissue factors, collagen and certain metabolites or hormones such as adenosine diphosphate (ADP), adrenaline and thromboxane. The clotting mechanism makes use of two systems: (a) soluble factors in the blood which activate each other in a serial manner causing hydrolysis of fibrinogen to fibrin which forms an insoluble cross-linked network, and (b) the circulating thrombocytes (platelets) which respond to the activating stimuli by releasing their own activators and by aggregating with each other. In normal clotting the soluble and platelet systems interact, with activation of one reinforcing the activation of the other. Abnormal activation of these systems can give rise to peripheral obstructive diseases. While the pathogenesis is very complex, current models involve a lesion of the vein or artery wall, local activation of the clotting system, recruitment of activated soluble factors and platelets into the region, homeostasis, local ischemia, and reinforced activation recruitment.

The platelet plays a central role in the formation and extension of clot in both venous and arterial thrombosis. In venous thrombosis, the activation of platelet initiates shape changes and release reactions of platelet contents such ADP, arachidonic acid derivatives, clotting factors which promote platelet recruitment and aggregation and activate coagulation cascade leading to fibrin formation. The activated platelet also provides an activated surface (platelet factor III) which serves as a binding site for soluble clotting factors thereby increasing their interaction and further accelerating the rate of fibrin formation.

Current therapy for venous thrombosis relies mainly on the inhibition of fibrin formation; little attention was given to inhibition of the platelet which plays central role in activation. Conventional therapy for venous thrombosis makes use of heparin which actively neutralizes several of the activated soluble clotting factors. Conventional therapy also makes use of the so-called "oral anticoagulants" (dicumarol and related compounds) which inhibit the synthesis of these factors. Direct platelet activation is not affected by these drugs. In arterial thrombosis, platelets adhere to injured or diseased vessel wall and transform their shapes, release ADP and other platelet granule content, convert arachidonic acid to thromboxane $A_2$, which promotes more platelet aggregation and vasoconstriction and consolidation of platelet plugs. The use of antiplatelet drugs is, therefore, the mainstay of treatment and prevention of arterial thrombosis. Two classes of drug target the platelet and are used to treat arterial thrombosis: aspirin and dipyridamole. Aspirin inhibits the activation of arachidonic acid, which is one of the pathways for platelet activation. This offers some protection against activation. Dipyridamole is a phosphodiesterase inhibitor which increases the platelets' cyclic AMP level. This offers further protection against activation. Extensive clinical trials on the use of these agents in arterial thrombosis showed minimal therapeutic effects.

$Ca^{2+}$ Entry Blockers Are Effective Anticoagulants: The above information suggests that it would be useful to be able to further inhibit the platelet contribution to the aggregation process. The present invention shows that increases in cytoplasmic $Ca^{2+}$ concentration are central to the activation process. For instance, it has been demonstrated that platelets from patients with peripheral obstructive diseases have defects in their $Ca^{2+}$ handling which gives rise to higher cytoplasmic and sequestered $Ca^{2+}$ levels. This results in increased probability of recruitment of the platelet into the growing thrombus or diseased area. This $Ca^{2+}$ handling defect can be corrected according to the present invention by medication with $Ca^{2+}$ entry blockers; clinical improvement in the patient results. Currently-available methods are not capable of assessing these abnormalities because such testing methods are too insensitive to the $Ca^{2+}$ handling defect. As disclosed herein, the action of the $Ca^{2+}$ channel blockers is readily demonstrated using a fluorescent probe technique for the measurement of platelet-sequestered $Ca^{2+}$.

Discovery of $Ca^{2+}$ Entry Blockers; Cardiac and Smooth Muscle Effects: A large number of compounds, termed generically "$Ca^{2+}$-channel blockers" has seen widespread use in the control of angina and treatment of myocardial infarction. These are presently divided into three groups: (1) nifedipine and related 1,4-dihydropyridines, (2) verapamil and methoxyverapamil (D600), and (3) diltiazem and cinnarizine and related diphenylmethyl alkylamines. A cardiac-inhibitory function of verapamil was discovered by Fleckenstein (Fleckenstein, A., Tritthart, H., Fleckenstein, B., Herbst, A. and Grun, G., A new group of competitive Ca antagonists (Iproveratril, D600, Prenylamine) with high potent inhibitory effects on excitation-contraction coupling in mammalian myocardium (1969), Pfluegers Arch. 306:R25) who showed that this compound had inhibitory actions similar to the removal of extracellular $Ca^{2+}$. Subsequently, he demonstrated that this action was shared with methoxyverapamil and nifedipine. He suggested that the compounds be termed "$Ca^{2+}$ antagonists" and showed that the effects of these agents were to block the slow inward $Ca^{2+}$ current during systole. Subsequently, the compounds were shown to inhibit $Ca^{2+}$ influx into smooth muscle. These properties make the compounds very suitable for control of angina and treatment of myocardial infarction. The $Ca^{2+}$-channel blockers apparently exert their actions primarily at membrane potential-dependent $Ca^{2+}$ channels. In smooth muscle, which can be stimulated both by membrane depolarization and noradrenaline or acetylcholine, the $Ca^{2+}$ channel blockers are generally less effective against receptor-activated channels, sometimes requiring four orders of magnitude higher doses for 50% effectiveness. The literature shows that a given $Ca^{2+}$ channel blocker will show different $ED_{50}$s for different tissues and that a given tissue will have different $ED_{50}$s for different channel blockers.

The present invention deals with the use of calcium channel blockers in diseases arising from platelet hyperactivation. Contemporary knowledge in the art has failed to establish a definite effect of the calcium channel blockers on the platelet and has a number of explanations each attributable to the conditions of the study and intricacies of the tested system. The test of $Ca^{2+}$-handling abnormalities used in the present application is more specific to the diseased state and to the mechanism of progression of peripheral obstructive disease.

We have discovered and hereby disclose method of treating peripheral obstructive diseases in patients requiring such treatment in which a $Ca^{2+}$ channel blocker is administered to the patient for a period of time and in therapeutic quantities effective to relieve the disease symptoms and mitigate or remove the obstruction.

Also disclosed is a sensitive diagnostic procedure for assessing defection, abnormal $Ca^{2+}$ handling of platelets which is indicative of certain peripheral obstructive diseases and, in turn, a means to assess a patient's response to $Ca^{2+}$ channel blockers in the therapy of such diseases. Method for correcting the $Ca^{2+}$ handling characteristics of blood platelets are also described.

DETAILED DESCRIPTION OF THE INVENTION

Mechanism by which Nifedipine and Other $Ca^{2+}$ Channel Blockers Correct Diseases Involving Platelet Hyperactivation: While not wishing to be bound to any theory or mode of operation, our work demonstrates the efficacy of nifedipine in reducing the internal $Ca^{2+}$ levels in circulating platelets in patients with thromboembolic disease which, in turn, returns the platelet aggregation characteristics to normal. The rationale is based on the following unique observations: (a) the level of $Ca^{2+}$ stored in the organelles of the platelet can be readily determined by a simple technique using the fluorescence of the probe chlorotetracycline (CTC) which is coaccumulated with the sequestered $Ca^{2+}$ (Haynes, D. H., Jy, W., Ahn, Y. S. and Harrington, W. F. (1983), The use of Nifedipine in the treatment of thrombosis, U.M. PHARM-Rept. 83/1 #PB 84 129055, National Technical and Information Service and Jy, W. and Haynes, D. H. (1984), Intracellular $Ca^{2+}$ storage and release in the human platelets: chlorotetracycline as a continuous monitor (submitted for publication)), (b) that the level of sequestered $Ca^{2+}$ observed under non-stimulated or sub-threshold stimulated conditions increased with increasing $Ca^{2+}$ permeability of the plasma membrane, (c) that the resting level of sequestered $Ca^{2+}$ is elevated in patients suffering from thrombosis or related platelet disorders (d) that the process of physiological activation of the platelet depends on the release of internally sequestered $Ca^{2+}$ to the cytoplasm (Fuster & Cheseboro, 1981; Haynes et al, 1983; Jy and Haynes, 1984) as well as $Ca^{2+}$ influx across the plasma membrane, (e) that increased levels of sequestered $Ca^{2+}$ render the platelet more sensitive to stimulation by physiological agents, (f) that treatment of the patients with $Ca^{2+}$ channel blockers decreases both the levels of sequestered $Ca^{2+}$ and the rate of $Ca^{2+}$ influx both under subcritical and critical levels of stimulation, (g) that the circulating platelets are probably subjected to a large range of subcritical activating stimuli in the circulation of the thrombosis patient and that this opens a fraction of the $Ca^{2+}$ channels, increases the cytoplasmic $Ca^{2+}$ concentration, increases the levels of stored $Ca^{2+}$ and generally predisposes the platelet to activation in the region of the growing thrombus where the strength of the stimuli is near critical or supercritical, (h) that treatment of the patient with calcium channel blockers antagonize the effects of chronic subcritical stimulation (the most important effect shown in the applicants' work) and increases the threshold for recruitment of platelets into the growing thrombi, (i) that this protective effect is not measured sensitively by the currently available aggregation tests, such as ADP- or collagen-stimulated aggregation, and (j) that the effects described above give rise to an increased rate of clinical improvement.

Figure 1:
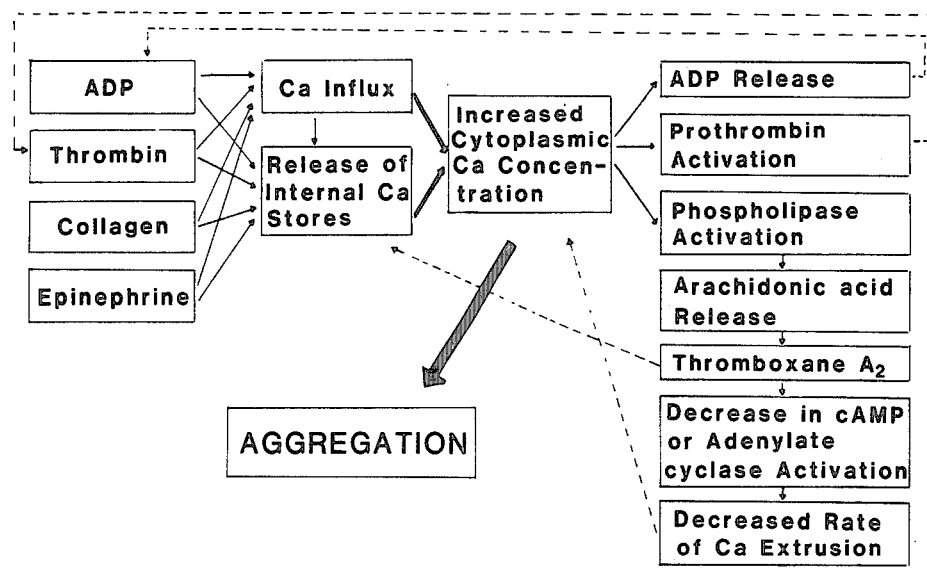
FIG. 1 is a diagram (after Fuster, V. and Cheseboro, J. H. (1981), Current Concepts of Thrombogenesis: Role of Platelets, Mayo Clin. Proc. 56:102–112) showing the mechanisms by which platelets are activated. The primary activating factors shown on the left give rise to calcium influx into the cytoplasm and calcium release to the cytoplasmic from internal stores. This is the primary intracellular trigger for aggregation. The directions of action are given by the arrows. The dotted lines indicate positive feedback interactions. For example, increased cytoplasmic calcium concentration brings about ADP release which, in turn, brings about increased cytoplasmic calcium concentration.

The effectiveness of the $Ca^{2+}$ channel blockers in reducing the rate of platelet depositions onto thrombi derives from the central role which $Ca^{2+}$ plays in the activation process. The novelty of the present invention is demonstrated by the fact we have demonstrated that medication with the calcium channel blockers reduce the levels of stored and cytoplasmic calcium. It was not possible to observe direct effects on the deranged platelets using standard methods since these rely on massive stimulation during the course of the measurement, and thus obscure the difference between abnormal and normal platelets. On the other hand, the CTC test described below and our studies with the cytoplasmic $Ca^{2+}$ indicator Quin 2 showed a direct and dramatic effect which has extremely good predictive value with regard to the course of the patient's symptoms. Reference to FIG. 1 shows that the levels of stored and cytoplasmic $Ca^{2+}$ are primary determinants of the process of aggregation. This figure summarizes the mechanisms discussed by Fuster and Cheseboro (1981) in their review article on the mechanism of thrombosis formation and platelet aggregation. The figure shows that all of the physiological stimulants, i.e., ADP, thrombin, collagen and epinephrine, cause activation by increasing $Ca^{2+}$ influx and by releasing internally stored $Ca^{2+}$. The ratio between $Ca^{2+}$ influx and release of the stores may differ with the different activators. However, $Ca^{2+}$ influx does bring about increased cytoplasmic $Ca^{2+}$ concentrations which can cause release of internally stored $Ca^{2+}$. Elevated cytoplasmic $Ca^{2+}$ also brings about ADP release and prothrombin activation which further stimulate $Ca^{2+}$ influx into the platelet and neighboring platelets, thereby increasing the degree of aggregation and recruiting new platelets into the clot. The autocatalytic nature of this process would be expected to give rise to a sharp dependence on cytoplasmic $Ca^{2+}$ concentration.

The platelet also contains a prostaglandin system which seems to serve as a mechanism for strengthening the response to stimulation. The $Ca^{2+}$-induced phospholipase liberates arachidonic acid which is converted to thromboxane $A_2$ which is believed to increase the cyclic AMP level of adenylate cyclase activity resulting in the decreased rate of $Ca^{2+}$ extrusion. This would make it more difficult for the platelet to lower the cytoplasmic $Ca^{2+}$ level and would thus decrease the probability that a stimulated platelet could recover normal $Ca^{2+}$ homeostasis.

$Ca^{2+}$ channel blockers suitable for use in the present invention are selected from the following representative compounds:

Nifedipine. Procardia ®, Pfizer Laboratories, Pfizer, Inc. (see The Merck Index, 10th Edition, registry No. 6374 and U.S. Pat. No. 3,485,847)
Diltiazem, Cardizem ®, Marion Laboratories, Inc. (see The Merck Index, 10th Edition, registry No. 3189 and U.S. Pat. No. 3,562,257)
Verapamil, Calan ®, Searle Pharmaceuticals (see The Merck Index, 10th Edition, registry No. 9747 and U.S. Pat. No. 3,261,859)
Isoptin ®, Knoll Pharmaceutical Company
Niludipine (BAY A 7168), Bayer AG
Nimodipine (BAY E 9736), Bayer and Miles Pharmaceuticals
Lidoflazine, Janssen Pharmaceuticals
Bepridil, C.E.R.M, Roim, France, Wallace Laboratories
Prenylamine, Farbenwerke Hoechst or Hoechst Roussel Pharmaceutical Inc., Summerville, N.J. 08876
Flunarizine, Ortho Pharmaceuticals, Janssen Pharmaceuticals
Fendiline, Dr. Thieman, GmbH
Caroverine, Mitsubishi Chemical Industries, Ltd.
Cinnarizine, Stugeron ®, Janssen Pharmaceutical Ltd., U.K.
Perahexiline, Merrill International
Terodiline, Bicor ®, Kabr Vitrum A.B., Sweden
Nitrendipine, Miles Pharmaceuticals
Nisoldipine, Miles Pharmaceuticals
Nicardipine, Syntex Diseases arising from platelet hyperactivation as described herein include the following: peripheral vascular occlusive diseases, thrombosis, stroke, vasculitis, myelofibrosis, vasculitis, immune thrombocytopenia, venous thrombosis, arterial thrombosis, collagen-vasculitis, vasculitis lupus, and platelet disorders.

Other conditions believed to be responsive to the treatment of the present invention include auto immune disorders involving platelets, other peripheral vascular diseases involving platelets, and atherosclerosis. Understanding the fundamental methodology one skilled in this art will recognize other conditions and disease states susceptible to treatment with $Ca^{2+}$ channel blockers.

Comparison with Conventional "Antiplatelet" Therapy Consisting of Dipyridamole or Aspirin: Consideration of FIG. 1 shows why treatment with these antiplatelet drugs is not completely successful and why the standard in vitro tests used to measure calcium channel blocker efficacy as an antiplatelet drug have been unsuccessful. The current antiplatelet drugs work only by protecting against the cyclic AMP effects "which give rise to a decreased rate of $Ca^{2+}$ extrusion" (Fuster and Cheseboro, 1983). Aspirin works by inhibiting the conversion of the archidonic acid to thromboxane $A_2$ step. Dipyridamole works by increasing the cyclic AMP level. Both of these agents give rise to an increased rate of $Ca^{2+}$ extrusions when compared to untreated platelets. However, these agents do not decrease the rate of $Ca^{2+}$ influx. The $Ca^{2+}$ extrusion system is easily overwhelmed in the course of normal activation and it is probably just as easily overwhelmed in the abnormal platelet by weaker stimuli.

The applicants' work shows that the $Ca^{2+}$ channel blockers are able to diminish $Ca^{2+}$ influx into the diseased platelets. This property has not been directly assessed by other workers because $Ca^{2+}$ influx studies are more difficult to do. Also, standard activation studies are considered by most workers to be superior since they encompass the overall reaction. But, as mentioned above, the autocatalytic nature of the activation process tends to make all activation processes approach the same maximal level regardless of strength of the initial stimulus and despite the possible blocking of a large fraction of the channels. Almost complete blocking of all of the channels would be necessary to suppress effects of a super-threshold stimulus. Significant effects of the channel blockers on diseased platelets might have been seen if the level of stimulus threshold had been specifically tested, but this type of detailed study is not common practice and is beyond the present state of the art. The novelty of the findings reported herein lies in both detection of the abnormality in the demonstration of its correction. The ability of channel blockers to decrease the $Ca^{2+}$ influx and thus reduce the levels of releasable $Ca^{2+}$ is readily seen by the chlorotetracycline (CTC) method. The return of the nifedipine-treated platelets to normal $Ca^{2+}$ homeostasis is shown to result in an increase in the rate of reversal of the disease.

EXPERIMENTAL METHODS

The Chlorotetracycline Method of Assessing Plasma Membrane Leakiness: The $Ca^{2+}$ sensitive fluorescent probe chlorotetracycline (CTC) has been applied widely in biological systems to monitor active $Ca^{2+}$ transport. A large increase in fluorescence accompanies active $Ca^{2+}$ transport. (Caswell, A. H. and Hutchison, J. P. (1971), Visualization of Membrane-bound cations by a fluorescent technique, Biochem. Biophys. Res. Commun. 42:43–49; Caswell, A. H. (1972), The migration of divalent cations in mitochondria visualized by a fluorescent chelate probe, J. Memb. Biol. 7:345–364; Caswell, A. H. and Warren, S. (1972), Observation of calcium uptake by isolated sarcoplasmic reticulum employing a fluorescent chelate probe, Biochem. Biophys. Res. Commun. 46:1757–1763; and Gershergorn, M. C., and Thaw, C. (1982), TRH mobilizes membrane calcium in thyrotropic cells as monitored by chlorotetracycline, Am. J. Physiol. 243:E298–E304). Our previous work with isolated sarcoplasmic reticulum (SR) has shown that CTC fluorescence can be used to report the free internal $Ca^{2+}$ concentration obtained by the $Ca^{2+}$-$Mg^{2+}$-ATPase pump (Millman, M. S., Caswell, H. H. and Haynes, D. J. (1980), Kinetics of chlorotetracycline permeation in fragmented ATP-ase-rich sarcoplasmic reticulum, Membrane Biochemistry 3:291–315). We have modeled the phenomenon showing that CTC accumulated in the organelle to an extent proportional to the free internal $Ca^{2+}$ concentration. The (Ca-CTC)+ complex binds to the internal surface of the organelle membrane. Thus the fluorescence increase is proportional to the free internal $Ca^{2+}$ concentration ($[Ca^{2+}]_i$) in the SR lumen.

Figure 2:
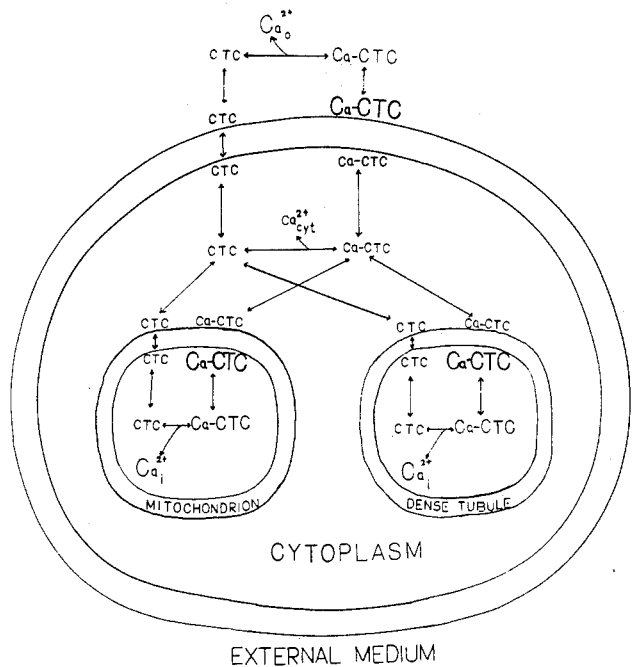
FIG. 2 is a schematic diagram showing how the fluorescent probe chlorotetracycline (CTC) indicates accumulation in the dense tubules. The probe is capable of making calcium complexes both in the aqueous base, in the cytoplasm and in the lumenar (aqueous spaces) of the dense tubules and mitochondria. These complexes make a small contribution to the total sample fluorescence. These calcium complexes combine to the corresponding membrane surfaces. The fluorescence contribution of the membrane bound $Ca^{2+}$-CTC species is much higher than that of the corresponding aqueous species. The relative size and contribution of the fluorescent signal from each species is indicated by the relative size of the symbols. Uncomplexed CTC can cross the membranes; $Ca^{2+}$-CTC cannot; thus the CTC accumulates in regions of high $Ca^{2+}$ concentration and its fluorescence is a measure of the free $Ca^{2+}$ concentration there.

Our studies of the human platelet have shown that the $Ca^{2+}$-sensitive fluorescent probe CTC can be easily used to monitor the $Ca^{2+}$ movement in human platelets. As shown in FIG. 2, (Ca-CTC)+ complex accumulates in the dense tubules and mitochondria. The fluorescence signal has been shown to be a linear measure of the level of free $Ca^{2+}$ in the dense tubules and in the mitochondria with probe sensitivity to $Ca^{2+}$ concentrations in these organelles in the millimolar range. Experiments using low concentrations of the $Ca^{2+}$-ionophore A23187 showed that the level of free internal $Ca^{2+}$ in the organelle depends upon the cytoplasmic level which in turn depends upon the passive permeability of the plasma membrane. CTC in the cytoplasmic compartment does not report to changes in the cytoplasmic $Ca^{2+}$ concentration ($[Ca^{2+}]cyt$), which is held in the micromolar to sub-micromolar range by an extrusion system located in the plasma membrane. Thus plasma membrane leakiness or low levels of activation of the $Ca^{2+}$ channels of the plasma membrane will increase the cytoplasmic $Ca^{2+}$ level, increasing the dense tubular and mitochondrial sequestered $Ca^{2+}$ level and increasing the CTC signal.

Quality Control and Reproducibility: The quality of the normal platelet samples from healthy volunteers was routinely determined before experimentation. No spontaneous aggregation was found upon stirring. All normal samples had to show normal aggregation kinetics. The $ED_{50}$ for collagen and ADP-induced aggregation of normal platelets was 15—15 ug/ml and 1–3 uM, respectively. This compares with literature values of 30 ug/ml (Chesney, C. M., Harper, E. and Colman, R. W. (1972), Critical role of the carbohydrate side chains and collagen in platelet aggregation, J. Clin. Invest. 51:2693–2701) and 3 uM (MacMillan, D. C. (1966), Secondary clumping effect in human citrated platelet rich plasma produced by adenosine diphosphate and adrenaline, Nature (London), 211:140–144), respectively. The CTC assay itself was also used as a criterion of quality. The responses shown in FIG. 3 were observed to be more sensitive measures of platelet quality than the above-cited tests. After approximately 24 hours of storage, the slow amplitudes shown in FIG. 3 increase while the size of the response to A23187 decreases. As will be shown below, platelets isolated from patients suffering from thrombosis gave a CTC response typical of aged or A23187-treated platelets from normal samples.

Washed Platelet Suspension: Blood was drawn from patients and normal volunteers into ACD (acid-citrate-dextrose). The red cells were removed by centrifugation at 150 g for 15 minutes. Platelet concentrate was prepared by centrifugation at 900 g for 20 minutes. The platelets were washed twice and suspended in calcium and magnesium-free Tyrode solution containing 138 mM NaCl, 3 mM KCl, 5.5 mM glucose, 12 mM $NaHCO_3$, 0.4 mM $NaH_2PO_4$ with the pH adjusted to 7.35 with HCl and checked on an hourly basis according to the method of (Mustard, J. F., Perry, D. W., Ardlie, N. G. and Pakham, M. A. (1972), Preparation of suspension of washed platelets from humans, Br. J. Haematol. 22:193–204. This medium was used in all experimentation. The platelet concentrate was adjusted to give 20% transmittance for aggregation experiments and 50% transmittance for CTC fluorescence experiments. The data corresponded to 0.1 g/ml protein concentration. Storage was at room temperature and experimentation was at 37° centigrade. All samples were studied within 4 hours of blood drawing.

Fluorescence was measured in a Perkin Elmer (model MPF-3L) fluorometer equipped with a thermostatically controlled cell holder (T=37° C.). Reactions were carried out in a 1 cm plastic cuvette; mixing and stirring were achieved by a top mounted motor-driven plastic stirring rod. The excitation beam was polarized horizontally by a single polarizer (Chen, 1966) to reduce the light scattering effects. The fluorometer collects emitted light over a wide angle and control experiments showed that inner filter effects were negligible. In these experiments, the platelets were incubated with 10 μM chlorotetracycline at room temperature for 30 minutes before introduction into the fluorometer. The excitation and emission monochrometers were set at 380 nm and 520 nm, respectively.

Platelet aggregation was measured by the turbidimetric method (according to Born, G.V.R. (1962), Aggregation of blood platelets by adphosine diphosphate and its reversal, Nature 194: 927–929). The extent of platelet aggregation was determined by monitoring transmittance changes in a Beckman spectrophotometer (Model DB-G) at 600 nm. This instrument was similarly equipped with a plastic cuvette and motor-driven stirring rod.

Figure 3:
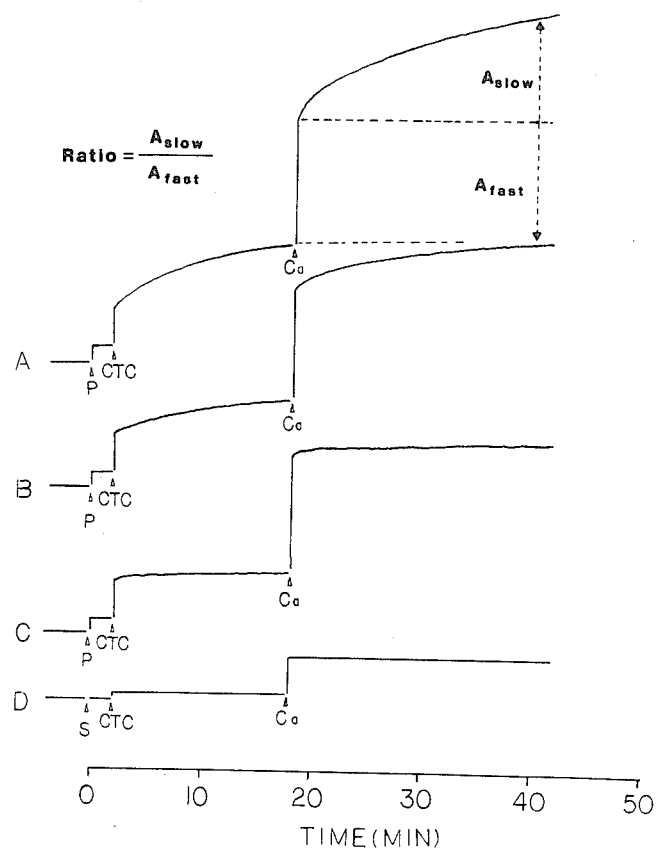
FIG. 3 shows four fluorometer records illustrating the use of the CTC fluorescent technique and the calculation of CTC ratio. Increasing fluorescence is plotted in the vertical direction and time is given in the horizontal direction. Curve A is for platelets from a patient with venous thrombosis; Curve B is for platelets from a healthy volunteer; Curve C is for metabolically-inhibited platelets from the same healthy volunteer; Curve D is a control experiment in which no platelets are added. The experiment was done at 37° C. with a Perkin Elmer (model MPF-3L) Fluorometer equipped with a top-mounted motor-driven plastic stirring rod and plastic cuvette. Excitation and emission wavelengths were 380 nm and 520 nm, respectively. The medium was calcium and magnesium-free Tyrode solution containing 138 mM CaCl, 3 mM KCl, 5.5 mM glucose, 12 mM $NaHCO_3$, 0.4 mM $NaH_2PO_4$ with the pH adjusted to 7.35. Abbreviations and final concentrations are: P = platelet suspension; S = saline; 10 uM CTC; 2 mM $Ca^{2+}$.

Abnormal Platelets Show Abnormal CTC Response, Indicating Plasma Membrane Leakiness to $Ca^{2+}$: FIG. 3 is a series of experiments showing that abnormal platelets have higher levels of $Ca^{2+}$ in their dense tubules and mitochondria than do normal platelets. The curves show thet typical CTC fluorescence response to $Ca^{2+}$ addition for abnormal (Curve A) and normal (Curve B) platelets. Curve B illustrates a standard protocol, showing the results of serial addition of platelets, CTC and $Ca^{2+}$. The platelet addition gives rise to only a small light scattering artifact. Addition of CTC results in a rapid rise in fluorescence, followed by a slow increase with a $t_{\frac{1}{2}}$ of 4-5 minutes. The rapid change is due to the fluorescence of CTC in the aqueous phase and CTC bound to the outer surface of the plasma membrane. At the low external $Ca^{2+}$ concentrations, the corresponding $Ca^{2+}$ complexes make only a small contribution (cf. FIG. 2). The slow fluorescence increase has been shown to arise primarily in the binding of CTC and its $Ca^{2+}$ complexes to the inner surfaces of the organelles. The control experiments (Curve D) in the absence of platelets show that only 20-25% of the rapid response is due to CTC in the aqueous phase. No slow phase was observed.

Information about $Ca^{2+}$ handling by the platelets is obtained by observing the response to the $Ca^{2+}$ addition. Curve B shows that the addition of $Ca^{2+}$ to a final concentration of 2 mM gives rise to two phases of increase: (a) An instantaneous phase corresponding to the binding of the $(Ca-CTC)^+$ complex on the outside surface, and (b) a slower plase ($t_{\frac{1}{2}}$-6-8 min) due to increases in internal $Ca^{2+}$ which, in turn, give rise to increase $(Ca-CTC)^+$ binding to the internal membranes. The slow phase has been shown to be due to active uptake of $Ca^{2+}$ from the cytoplasm into the mitochondria and dense tubules. It is largely blocked by 1 hour pretreatment with $NaN_3$, oligomycin and trifluoperazine (Curve C).

amplitude. A similar result (not shown) is obtained when a normal platelet sample was pretreated with 20 nM A23187, a $Ca^{2+}$ ionophore which makes plasma membrane permeable to $Ca^{2+}$ (Jy and Haynes, 1984). Both the mechanism of the CTC response and the comparison show that the abnormal platelets have an increased uptake of $Ca^{2+}$ into the organelles. Experiments using the cytoplasmic $Ca^{2+}$ monitor Quin 2 show that the abnormal platelets have increased cytoplasmic $Ca^{2+}$ levels. Experiments, reported below, show that the plasma membrane defect can be corrected by administration of $Ca^{2+}$ channel blockers is vitro and in vivo.

Platelets from Patients with Thrombosis Show Increased $Ca^{2+}$ Uptake: The ratio of the slow change to the fast change observed upon $Ca^{2+}$ addition (FIG. 3) was taken as a measure of the $Ca^{2+}$ handling abnormality. Table I shows that the value of this parameter in the thrombosis patients is 2.3-2.5 times the level observed in healthy controls. Parameter I is the ratio of the amplitudes of the slow phase to the fast phase. This parameter controls for possible differences in platelet composition.

Experiments show a large elevation of organelle-associated $Ca^{2+}$ in platelets from patients with arterial or venous thrombosis. Table I shows that stimulation with collagen (Parameter II) produces a correspondingly larger decrease in fluorescence, as compared to normal controls (1.3-2.4 fold). This suggests that the dense tubules in these abnormal platelets are capable of releasing more $Ca^{2+}$ to the cytoplasm, suggesting a greater sensitivity towards activating agents. Table I also demonstrates that the abnormal platelets show a greater transmittance when stimulated by collagen. However, this increase (abnormal/normal equals 1.3-1.5) was only marginally siginificant due to the large variability of the abnormal patients. No differences in aggregation rate were observed. This supports the above observation that standard tests are insensitive to hypercoagulability disorders and that the CTC technique is a much more sensitive measure of the same.

TABLE I

| COMPARISON OF THE CALCIUM HANDLING ABILITY AND AGGREGATION BETWEEN NORMAL CONTROL AND THROMBOSIS PATIENTS | | | |
|---|---|---|---|
| | Normal Control n = 26 | Arterial Thrombosis n = 13 | Venous Thrombosis n = 18 |
| I. $Ca^{2+}$ jump slow phase/fast phase | 0.35 ± 0.08 | 0.88 ± 0.27 | 0.79 ± 0.29 |
| II. Collagen stimulated $Ca^{2+}$ release (F) | −12.8 ± 1.1 | −18.4 ± 1.6 | −16.9 ± 2.1 |
| III. Aggregation (ΔT %) | 18.5 ± 3.2 | 27.6 ± 7.0 | 24.8 ± 4.6 |

Collagen stimulated $Ca^{2+}$ release and aggregation were evoked by addition of 20 μg/ml collagen to platelets in Tyrodes solution containing 2 mM $Ca^{2+}$.

Previous work has shown that the cytoplasmic level is coupled to the external level by pumps and leaks in the plasma membrane. This, in turn, is coupled to the mitochondrial and dense tubular levels. Thus, elevating the external $Ca^{2+}$ concentration increases the rate of $Ca^{2+}$ influx and increases the cytoplasmic level. This allows for increased uptake by the organelles.

We have found that patients suffering from thromboembolism (venous and arterial) and immune thrombocytopenia, vasculitis and myelofibrosis have elevated levels of $Ca^{2+}$ in their dense tubules and mitochondria, indicating a leaky plasma membrane. Curve A shows a result obtained with a patient suffering from arterial/venous thrombosis. The fast phases are not affected by the disease, but the slow phases are greatly increased in $Ca^{2+}$ Handling Abnormalities of Patient with Thrombosis Is Correctable by In Vitro Treatment with A Nifedipine Analog: Table II shows that the abnormal CTC response of a patient suffering from arterial and venous thrombosis (Patient A) was correctable by treatment with a nifedipine analog in vitro. The isolated platelets were preincubated with the calcium entry blocker Y108-068 (a nifedipine analog) at 50 uM concentration for 30 minutes and were then tested for the three CTC parameters. The table shows that both the CTC ratio and the collagen-stimulated $Ca^{2+}$ release were returned to normal values by the $Ca^{2+}$ channel blocker.

Platelet aggregation studies on this sample showed normal extents of aggregation stimulated by ADP and collagen for this patient. The effect of Y108-068 on the extent of aggregation was small.

Clinical Improvement with Nifedipine Administration in A Thrombosis Patient: Patient A: Below, we describe the clinical course of Patient A who was treated with nifedipine. Patient A was a 68-year old man with myelofibrosis and myeloid metaplasia and was suffering from recurrent deep vein thrombosis (DVT). He was presented to us with massive DVT involving his left thigh, the size of which was 4 times larger than the right with severe erythema, a large hemorrhagic bullae from ischemia. Venogram and CAT scan confirmed large thrombi in the left iliac and femoral vein. No abnormal mass was identified on the CAT scan. He also experienced pleuritic chest pain consistent with pulmonary emboli on the lung scan. Heparin therapy (10,000-20,000 unit/hr) did not improve the DVT. A filter was inserted to prevent further pulmonary emboli. While on heparin he developed another large DVT on the right thigh. DIC screens were negative. Coagulation studies showed prolonged PTT from heparin. Platelets were large and bizarre with a count of 100,000/cumm.

Patient A was administered the calcium channel blocker Procardia®(nifedipine) 10 mg T.I.D. As shown below, this resulted in dramatic improvement of both the $Ca^{2+}$ handling parameters of his plaetlets and of his condition. Table II shows that within 10 hours of initiation of nifedipine therapy, the CTC ratio and collagen-stimulated release parameters were within the normal range. Within 24 hours after nifedipine therapy, pain improved requiring less narcotics. Improvement of erythema, tenderness and swelling was obvious on the third day of therapy. In fifth day patient condition was improved to be transferred to the referring physician.

pine plus standard therapy brings about improvement in the $Ca^{2+}$ handling of the platelets while the standard therapy alone brings about no improvement. A total of 18 patients were studied. Their mean value of the CTC $Ca^{2+}$ handling parameter was 0.79±0.29. Eight patients were medicated with nifedipine (10-20 mg T.I.D.) and the course of improvement of calcium handling was monitored. The treatment brought the calcium handling parameter to normal values for all of the patients except one. The right-hand portion of the figure shows the course observed for four patients who did not receive nifedipine. In this group, none of the CTC ratios returned to normal within seven days.

Figure 5:
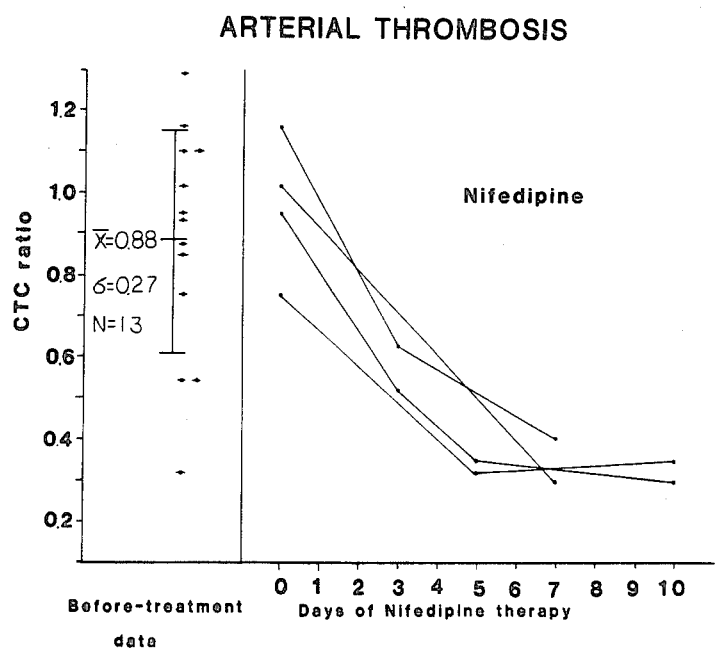
FIG. 5 shows the distribution of CTC ratios observed in 13 patients with arterial thrombosis and shows that the ratios are decreased by nifedipine therapy.
Figure 6:
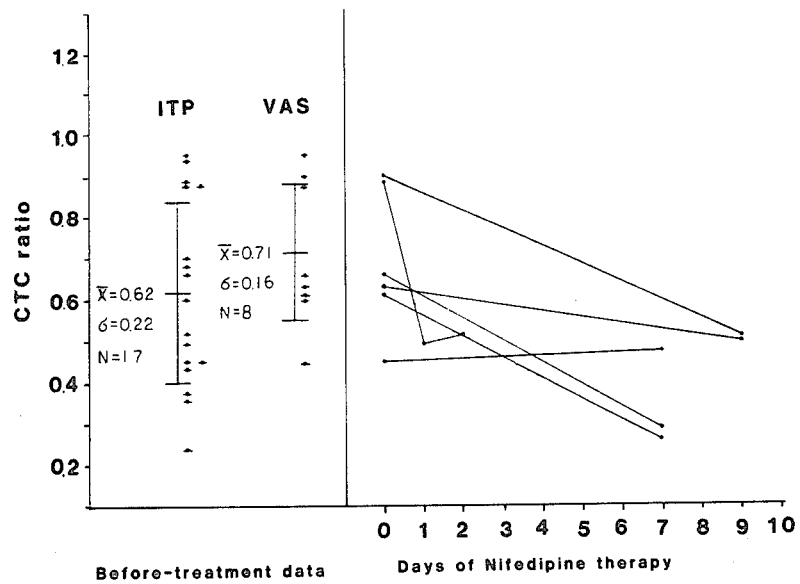
FIG. 6 shows the distribution of CTC ratios observed in 17 patients with immune thrombocytopenia and 8 patients with vasculitis. The figures shows that the CTC ratios are decreased by nifedipine therapy.

Medication with Nifedipine Normalizes $Ca^{2+}$ Handling in Patients with Arterial Thrombosis: Thirteen patients suffering from arterial thrombosis, some receiving antiplatelet drug such as persantin or aspirin, were studied. The mean value of the CTC parameter was 0.88±0.27. FIG. 5 shows the response of the CTC parameter to medication with nifedipine (10-20 mg T.I.D.) for four patients. Nifedipine reduced the CTC values, bringing them into the normal range within seven days for all patients. These results are shown in FIG. 6. Clinical improvement was observed in all patients.

Figure 7:
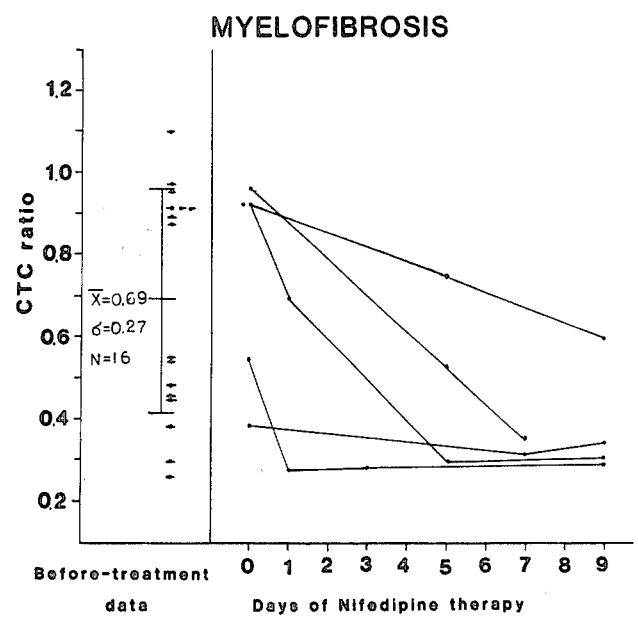
FIG. 7 shows the distribution of the CTC ratios observed in 16 patients with myelofibrosis and shows that the CTC ratios are decreased by nifedipine therapy.

Medication with Nifedipine Normalizes $Ca^{2+}$ Handling in Patients with Immune Thrombocytopenia and Vasculitis Lupus: The CTC test was applied to 17 patients with immune thrombocytopenia and eight patients with vasculitis associated with systemic lupus erythemotosis and other collagen vascular disorders. The mean values of their CTC ratios were 0.62±0.22 and 0.71±0.16, respectively. Six patients in these categories were medicated with nifedipine (10 mg T.I.D.). FIG. 7 shows that nifedipine therapy returned the CTC ratio to normal in three of these patients. Increased platelet counts were also observed in some of the pa-

TABLE II

CHANGES IN CALCIUM INFLUX AND RELEASE AFTER NIFEDIPINE TREATMENT: PATIENT A

| CTC Parameter | Control Group: mean ± S.D. (n = 26) | Patient Data: | | | |
|---|---|---|---|---|---|
| | | Pre-treatment | | Post-treatment | |
| | | −52 hrs. | −4 hrs. | 10 hrs. | 72 hrs. |
| calcium influx | | | | | |
| (a) (Ratio: slow/fast) | 0.35 ± 0.08 | 0.51* | 0.54*(0.28)** | 0.27 | 0.27 |
| (b) Collagen stimulated calcium release | −12.8 ± 1.1 | −37* | −26.5*(12.5)** | −12 | −12.5 |

The table gives data obtained with platelets isolated from Patient A at the indicated time and studied using the CTC technique. The amplitude is tabulated for the slow phase of fluorescence increase observed upon addition of 2 mM calcium platelets (0.05 mg protein/ml) preincubated with 10 μM CTC. Parameter (b) is the ratio of amplitude of this phase to the corresponding rapid phase. Parameter (c) is the decrease in fluorescence observed upon addition of collagen to a final concentration of 20 gm/ml.
*Significantly greater than control group (P < 0.05).
**Result obtained with in vitro treatment with calcium blocker Y108-068 at 50 μM concentration.

The correlation of the CTC response of the isolated platelets with clinical improvement supports the further use of the CTC test as a measure of normalization of the platelet $Ca^{2+}$ homeostasis by this drug. Below, we report the results of treatment of a large number of patients suffering from peripheral obstructive diseases. The results show improvement of the $Ca^{2+}$ handling after nifedipine treatment and lack of such improvement when nifedipine is not administered.

Figure 4:
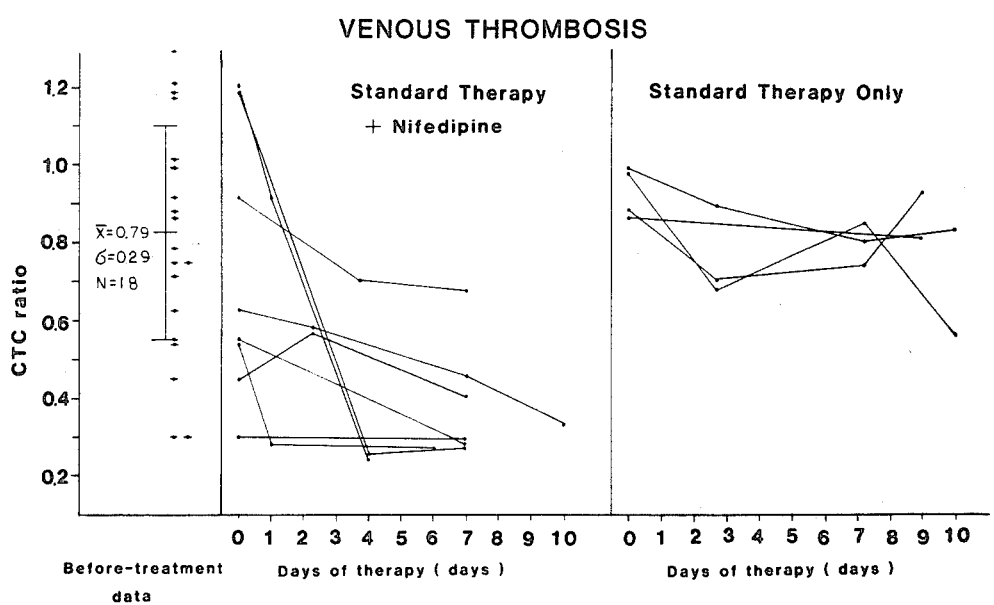
FIG. 4 shows the distribution of the CTC ratios observed in 18 patients with venous thrombosis. This figure shows the decrease in the CTC ratio with nifedipine therapy and shows the lack of effect of standard therapy (heparin or dicoumarol) alone.

Medication with Nifedipine Normalizes $Ca^{2+}$ Handling in Patients with Deep Vein Thrombosis: Following the initial studies with Patient A, 18 patients with deep vein thrombosis were studied. These patients were receiving standard therapy consisting of heparin or oral anticoagulants. FIG. 4 shows that treatment with nifeditients of this group.

Medication with Nifedipine Normalizes $Ca^{2+}$ Handling in Patients with Myelofibrosis: The CTC test was applied to 16 patients with myelofibrosis. The mean value of the CTC ratio was 0.69±0.27. Five patients were medicated with nifedipine (10-20 mg T.I.D.). This treatment normalized the CTC $Ca^{2+}$ handling parameter in four of the five patients, measured at seven days (FIG. 7). The treatment also increased platelet counts in two of the patients.

Figure 8:
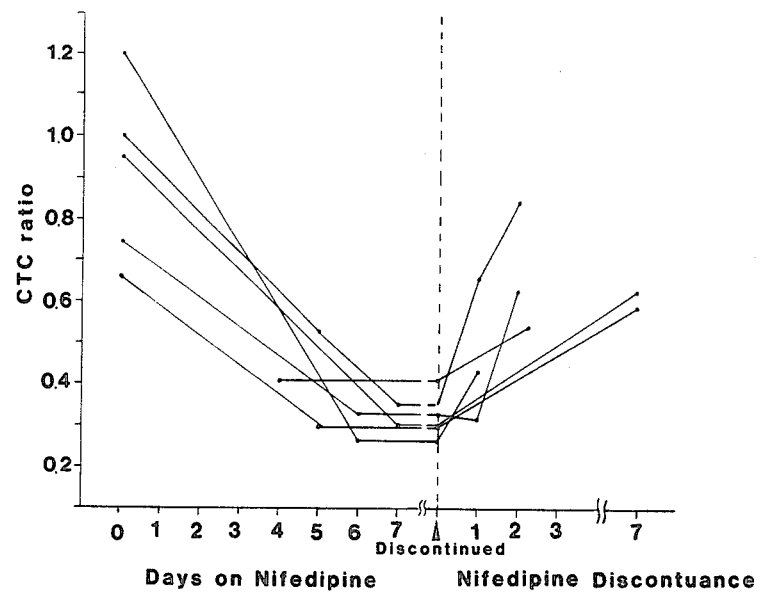
FIG. 8 shows that the nifedipine therapy-normalized CTC ratios are observed to increase towards abnormal values after discontinuation of nifedipine therapy.

FIG. 8 shows the results for six patients whose CTC values were normalized by nifedipine administration. After the value had stabilized in the normal range, nifedipine therapy was discontinued. The CTC parameter was observed to rise in all patients. This is further proof that the normalization of the $Ca^{2+}$ handling by these abnormal platelets is due to nifedipine, and is not a consequence of the standard therapy.

We claim:

1. A method of treating venous thrombosis comprising administering to a person having same an amount of nifedipine effective to relieve the symptoms of venous thrombosis and to restore substantially normal circulation in the involved blood vessel or vessels.

2. A method of treating arterial thrombosis comprising administering to a person having same an amount of nifedipine effective to relieve the symptoms of arterial thrombosis and to restore substantially normal circulation in the involved blood vessel or vessels.

3. A method of treating immune thrombocytopenia comprising administering to a person having same an amount of nifedipine effective to relieve the symptoms of immune thrombocytopenia and to restore substantially normal circulation in the involved blood vessel or vessels.

4. A method of treating vasulitis comprising administering to a person having same an amount of nifedipine effective to relieve the symptoms of vasulitis and to restore substantially normal circulation in the involved blood vessel or vessels.

5. A method of treating myelofibrosis comprising administering to a person having same an amount of nifedipine effective to relieve the symptoms of myelofibrosis and to restore substantially normal circulation in the involved blood vessel or vessels.

6. A method of treating a patient believed to have a thromboembolic disease who has increased $Ca^{2+}$ levels in the patient's blood platelets, comprising the steps of:
   (1) determining if the internal $Ca^{2+}$ levels in the patient's blood platelets are elevated by contacting a sample of the patient's platelets with chlorotetracycline, a detectable fluorescent probe, measuring the resulting fluorescence, comparing the value measured with the predetermined fluoresence assessed in a normal platelet, and, when the measured fluoresence is less than the predetermined fluoresence; and then
   (2) administering to the patient an amount of nifedipine effective to reduce the internal $Ca^{2+}$ levels in the platelets and thereby restore the platelet aggregation characteristics.

* * * * *